(12) United States Patent
Felk et al.

(10) Patent No.: US 7,684,060 B2
(45) Date of Patent: Mar. 23, 2010

(54) QUALITY-CONTROL METHOD FOR LAMINATED-FOIL PACKAGING SYSTEM

(75) Inventors: Günter Felk, Ulm-Einsingen (DE); Jörg Riekenbrauck, Schwendi (DE); Hans-Werner Bongers, Laupheim (DE)

(73) Assignee: Uhlmann Pac-Systeme GmbH & Co. KG, Laupheim (DE)

( * ) Notice: Subject to any disclaimer, the term of this patent is extended or adjusted under 35 U.S.C. 154(b) by 363 days.

(21) Appl. No.: 11/890,540

(22) Filed: Aug. 6, 2007

(65) Prior Publication Data

US 2008/0030745 A1    Feb. 7, 2008

(30) Foreign Application Priority Data

Aug. 5, 2006    (DE) .................. 10 2006 036 723

(51) Int. Cl.
*G01B 11/00*    (2006.01)

(52) U.S. Cl. ....................................... 356/626
(58) Field of Classification Search ................ 356/626
See application file for complete search history.

(56) References Cited

U.S. PATENT DOCUMENTS 5,582,665 A    12/1996    Eigen .......................... 156/69

2007/0296963 A1 *    12/2007    Parker et al. ............. 356/240.1

FOREIGN PATENT DOCUMENTS

JP    06027045    2/1994
JP    10267865    10/1998

\* cited by examiner

*Primary Examiner*—Gregory J Toatley, Jr.
*Assistant Examiner*—Amanda H Merlino
(74) *Attorney, Agent, or Firm*—Andrew Wilford

(57) ABSTRACT

In a sealing machine a pair of juxtaposed foils are sealed together at web regions having oppositely directed outer surfaces between a pair of dies, at least one of which is formed with an array of bumps that taper outwardly toward a respective one of the outer surfaces. The bumps press into the one outer surface and form therein permanent cavities of a predetermined imprint depth so as to bond together the foils at the web region. A quality of seal is determined by measuring after formation of the cavities surface features of the cavities at a level of the one outer surface of the respective foil, and calculating based on the measured surface features an imprint depth of the cavity.

7 Claims, 3 Drawing Sheets

QUALITY-CONTROL METHOD FOR LAMINATED-FOIL PACKAGING SYSTEM

FIELD OF THE INVENTION

The present invention relates to a laminated-foil packaging system. More particularly this invention concerns a quality-control method for such a system.

BACKGROUND OF THE INVENTION

In the mass-production of packages of small objects, in particular pills or similar pharmaceutical products, it is standard to form a base foil with an array of upwardly open blisters, to load at least one object into each of the blisters, and to bond a cover foil to an upper surface of the base foil so that it hermetically adheres to the base foil at webs between the blisters. This is all done continuously, with the foils moving through shaping, filling, and sealing stations at a constant travel speed. The base foil is typically a vacuum-formed thermoplastic, and the cover foil is typically a much thinner foil of metal and/or plastic that must be removed for access to the product by the consumer.

As detailed in U.S. Pat. No. 5,582,665 of Eigen, the quality of the seal between the foils at the webs between the blisters is critical. This seal is typically formed by passing the two foils between two dies having confronting outer surfaces. The lower die has an array of upwardly open pockets that fit with the blisters of the base foil, and the upper die has a surface formed with regions contacting the webs between the blisters with an array of small bumps or ridges that in fact impress a pattern into the upper cover foil. In U.S. '665 the bumps are of a shape tapering, that is becoming of smaller cross-sectional area, away from the die toward the workpiece, i.e. the foils, which may or may not have been fixed together into a laminate.

During the sealing operation with the shaped die or dies, the bumps actually are pressed into and even through the respective foil, almost always on the upwardly facing cover-foil side, and in many cases also on the downwardly facing base-foil side. Deformation is plastic and permanent with an imprint depth that can even exceed a thickness of the cover foil. This imprint depth has been determined to be critical to the web seal, for instance to meet the high standards of the European Commission, the Pharmaceutical Inspection Convention (PIC), and the US FDA, among others.

The imprint depth is a function of the composition, temperature, and thickness of the foil, the shape of the tool, the force applied to the tool, and other minor factors, so the imprint depth can vary when any of these factors changes. On the other hand experience has shown that the imprint depth must be a certain size for a proper seal. Too big and the foils might be pierced or damaged, too small and the foils are not adequately bonded. Since the primary factor determining imprint depth in a system is the pressure applied through the tool to the workpiece, it is standard in the prior art to use this factor—die pressure—to calculate imprint depth. This however does not take into account the other factors affecting imprint depth, the critical factor, so it is inaccurate at best. The actual seal might be inadequate, for example, because as a result of down time a portion of the workpiece gets very hot and is therefore very soft, so the imprint with a given pressure will be too deep.

OBJECTS OF THE INVENTION

It is therefore an object of the present invention to provide an improved quality-control method for a blister-packaging system.

Another object is the provision of such an improved quality-control method for a blister-packaging system that overcomes the above-given disadvantages, in particular that ensures that the actual seal quality, which as described above is closely related to imprint depth, can be determined and maintained at an ideal level.

SUMMARY OF THE INVENTION

This is achieved in a sealing machine where a pair of juxtaposed foils are sealed together at web regions having oppositely directed outer surfaces between a pair of dies, at least one of which is formed with an array of bumps that taper outwardly toward a respective one of the outer surfaces. The bumps press into the one outer surface and form therein permanent cavities of a predetermined imprint depth so as to bond together the foils at the web region. In accordance with the invention a quality of seal is determined by measuring after formation of the cavities surface features of the cavities at a level of the one outer surface of the respective foil, and calculating based on the measured surface features an imprint depth of the cavity.

With this method the imprint depth that is critical for seal quality and that is determined by comparison of the characteristics of the sealing tool and the foil, is ascertained in a simple manner using one of these directly dependent features. For this, there is no need to interrupt the sealing process and the measurement can extend to all bumps in a sealing seam so that there is therefore gapless quality control and thus further enhanced process security.

In the framework of the invention, it is particularly preferred that at least one edge of the bump imprint is detected. The advantage associated with this is comprised in that, depending on the bump geometry, which can be pyramidal, hemispherical, or conical, the length, the circumferential length or even the diameter through a circular edge, can be used for determining the imprint depth of the individual bump.

In the framework of the invention it is furthermore provided that the detection is optical. For one thing, this enables a contactless measurement method that furthermore is not susceptible to interference. In addition, given appropriately high temporal resolution, measuring that is independent of the advancing speed of the foil web can occur for an edge at each individual bump imprint. This represents optimum quality assurance for the entire sealing surface. Simple triangulating cameras or an optical detector with acute depth of field control can easily be used to measure the presence or absence of the outer surface, thereby determining where the edges of the cavities are so as to have all the information necessary to calculate imprint depth.

In order to prevent poor sealing quality due to only insufficient penetration of the bumps into the foil web, it is particularly advantageous that the derived or determined penetration depth of the bumps in the foil web is used as a regulating variable during the regulation of the sealing process, affecting an upstream process step. Using this, it is possible to use suitable actuators to adjust the sealing station during operation and thus process security can be enhanced and costs associated with rejects can be reduced.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
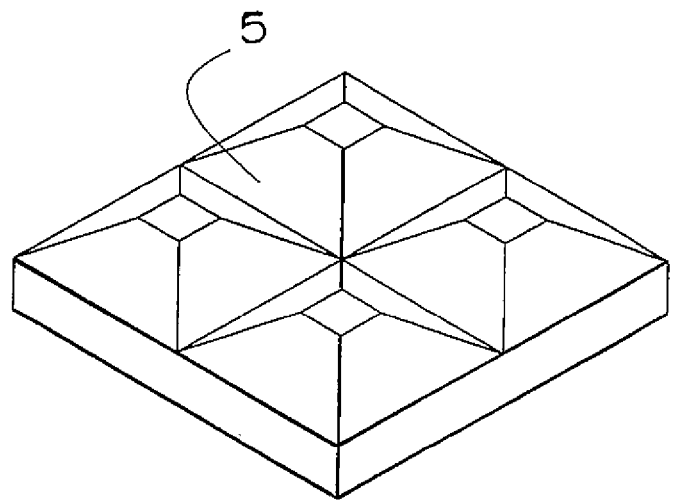
FIG. 1 is a perspective view of part of a tool usable in the system according to the invention.
Figure 2:
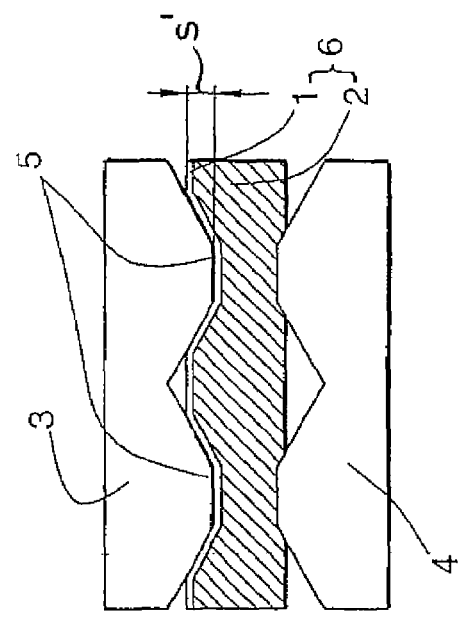
FIGS. 2 and 3 show the web-sealing method according to the invention with two different imprint depths.
Figure 3:
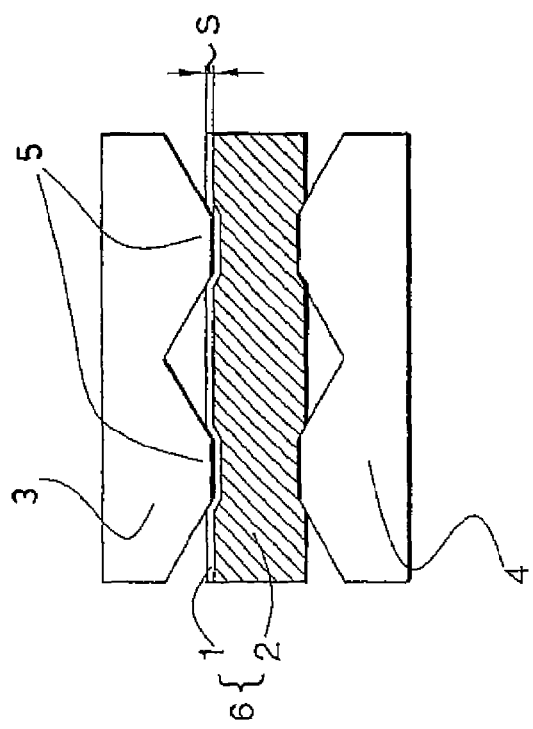
Figure 7:
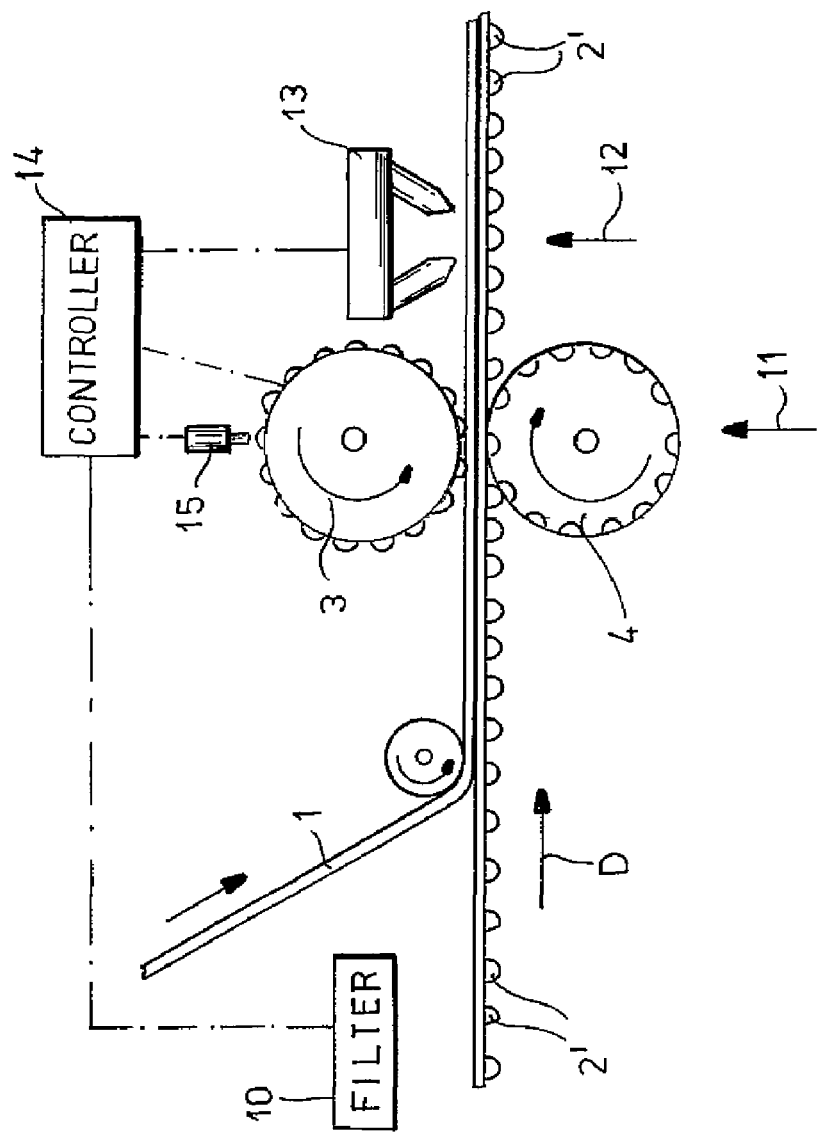
FIG. 7 is a schematic diagram illustrating the packaging system with the quality-control method according to the invention.

As seen in FIGS. 1-3 and 7 a cover foil 1 and a base foil 2 formed with blisters 2' are juxtaposed downstream of a filling machine 10 where unillustrated small objects such as pills are loaded into the blisters 2'. From the machine 10, the foils 1 and 2 are moved downstream in a horizontal travel direction D through a sealing station 11. Here, web regions between the blisters 2' are sealed together to a laminate 6 so as to hermetically separate the objects in the blisters 2'.

The station 11 is provided with a pair of sealing tools or dies 3 and 4 here shown as rollers rotatable about parallel horizontal axes one above the other, although it would be equally possible to provide traveling dies or purely vertically movable dies in a step-advance system. At least the top die 3 that engages the thinner cover foil 1 is formed on its surface regions engaging the web regions with an array of bumps 5. Here the bumps 5 are planar-sided frustopyramids, although straight-sided frustocones or other shapes would be possible, so long as the bumps 5 taper toward the respective. Here the lower roller die 4 is also formed with such bumps 5.

Figure 6:
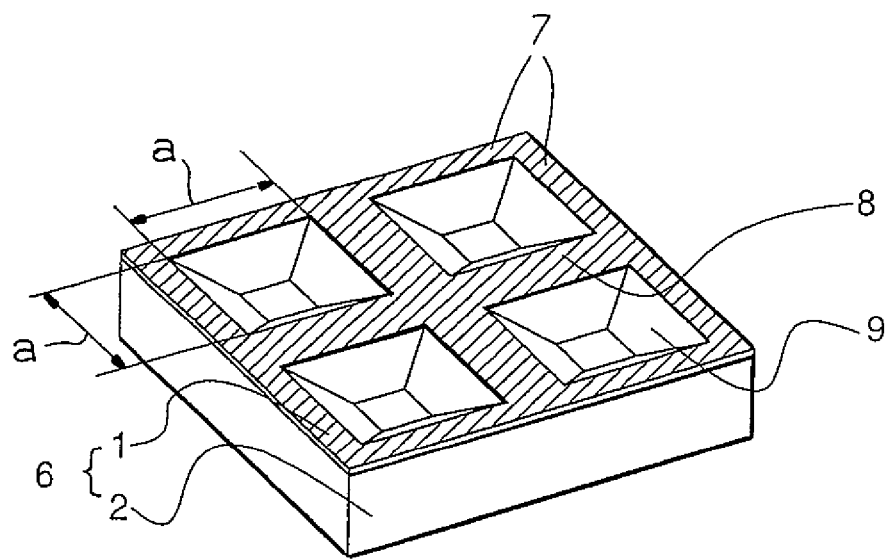
FIG. 6 is a perspective view of a small portion of the finished sealed workpiece in accordance with the invention.
Figure 4:
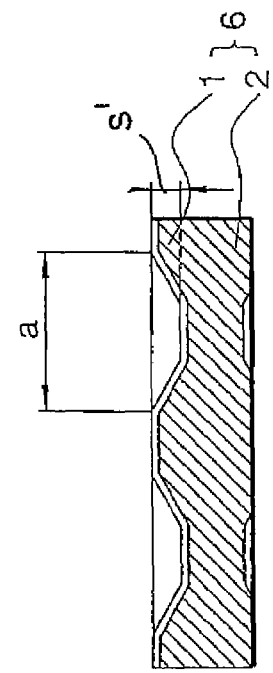
FIGS. 4 and 5 show the sealed workpieces after the sealing operation of respective FIGS. 2 and 3.
Figure 5:
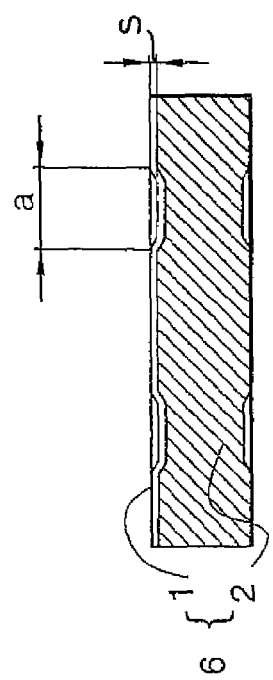

During operation as shown by FIGS. 2 through 6 the critical web regions of the cover foil 1 are plastically deformed by pressing the bumps 5 against them to form cavities 9 of a depth s of s' and of shapes complementary to the outer portions of the respective bumps 5 that formed them. As mentioned above, the depth s or s' is directly related to the seal quality, as determined experimentally.

Thus according to the invention downstream of the sealing station 11 is a quality-control station 12 having a camera 13 focused at the outer surface of the foil 2. This camera 13 in turn can detect edges 7 of the cavities 9 and report it to a controller 14 that can, based on stored data about the shape of the bumps 5, calculate the exact depth s or s'.

In turn this controller 14 is connected to the filler 10 and to an actuator 15 of the tool 3 so that it can affect the process when the calculated imprint depth s or s' goes outside an acceptable range or varies from a desired set-point level. For instance if the controller 14 detects that the seal is unacceptable because the imprint depth is too great or too small, it can stop filling of the pockets at 10 and vary the pressure exerted at the roller 3 until the right depth is restored, whereupon filling starts again. This way no product is wasted in unusable packaging, and the controlling is done in real time, with any correction taking place in accordance with current readings.

With this system the measurement of the area of a given cavity 9 is determined by detecting its edges 7. From this information an average width a of the cavity 9 can easily be calculated. Alternately a diagonal of a square or rectangular cavity could be calculated. Since the size and shape of the bumps 5 is fixed and known, it is a simple matter of geometry to determine the exact depth of the cavity 9.

We claim:

1. In a sealing machine where a pair of juxtaposed foils are sealed together at web regions having oppositely directed outer surfaces between a pair of dies, at least one of which is formed with an array of bumps that taper outwardly toward a respective one of the outer surfaces, the bumps pressing into the one outer surface and forming therein permanent cavities of a predetermined imprint depth so as to bond together the foils at the web region, a method of determining a quality of seal comprising the steps of:

measuring after formation of the cavities a surface area of the cavities at a level of the one outer surface of the respective foil; and calculating based on the measured surface an imprint depth of the cavity.

2. The method defined in claim 1, further comprising the step of:

conveying the foils in a travel direction between the dies.

3. The method defined in claim 1 wherein the surface area is measured by detecting positions of edges of the cavities.

4. The method defined in claim 3 wherein the edges are detected optically.

5. The method defined in claim 3 wherein the edges are detected optically by a camera.

6. The method defined in claim 1, further comprising the steps of:

conveying the foils in a travel direction through a processing station upstream of a sealing station incorporating the dies; and using the calculated imprint depth to control the processing station.

7. The method defined in claim 1 wherein the bumps are shaped as straight-sided frustums.

* * * * *